(12) United States Patent
Chiu et al.

(10) Patent No.: US 7,062,118 B2
(45) Date of Patent: Jun. 13, 2006

(54) MICRORING RESONATOR AND METHOD FOR MANUFACTURING

(75) Inventors: Raymond C. Chiu, Woodbury, MN (US); John E. Potts, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 51 days.

(21) Appl. No.: 10/623,215

(22) Filed: Jul. 18, 2003

(65) Prior Publication Data

US 2005/0013529 A1    Jan. 20, 2005

(51) Int. Cl.
G02B 6/26    (2006.01)
(52) U.S. Cl. .......................................... 385/15; 385/39
(58) Field of Classification Search ................. 385/15, 385/32, 39, 50
See application file for complete search history.

(56) References Cited

U.S. PATENT DOCUMENTS

| | | | |
|---|---|---|---|
| 5,926,586 | A | 7/1999 | Dragone et al. |
| 6,873,769 | B1 * | 3/2005 | Miyano et al. ............... 385/50 |
| 2002/0037132 | A1 * | 3/2002 | Sercel et al. .................. 385/30 |
| 2002/0114604 | A1 | 8/2002 | Dorn et al. |
| 2003/0118270 | A1 | 6/2003 | Miyano et al. |

FOREIGN PATENT DOCUMENTS

| WO | WO 86/02171 | 4/1986 |
|---|---|---|
| WO | WO 02/08815 | 1/2002 |
| WO | WO 03/036343 | 5/2003 |

OTHER PUBLICATIONS

Cai, M. et al., "5-Gbit/s BER Performance on an All Fiber-Optic Add/Drop Device Based on a Taper-Resonator-Taper Structure," *IEEE Photonics Technology Letters*, vol. 12, No. 9, pp. 1177-1179 (Sep. 2000).
Chin, M. K. et al., "Design and Modeling of Waveguide-Coupled Single-Mode Microring Resonators," *Journal of Lightwave Technology*, vol. 16, No. 8, pp. 1433-1446 (Aug. 1998).
Little, B. E. et al., "Microring Resonator Channel Dropping Filters," *Journal of Lightwave Technology*, vol. 15, No. 6, pp. 998-1005 (Jun. 1997).
Little, B. E. et al., "Ultra-Compact Si-SiO$_2$ Microring Resonator Optical Channel Dropping Filters," *IEEE Photonics Technology Letters*, vol. 10, No. 4, pp. 549-551 (Apr. 1998).
Rafizadeh, D. et al., "Waveguide-coupled AlGaAs/GaAs microcavity ring and disk resonators with high finesse and 21.6-nm free spectral range," *Optics Letter*, vol. 22, No. 16, pp. 1244-1246 (Aug. 15, 1997).

* cited by examiner

*Primary Examiner*—Sarah Song
(74) *Attorney, Agent, or Firm*—Stephen W. Buckingham

(57) ABSTRACT

A method for making a plurality of waveguide resonator devices is disclosed herein. The method includes fixing a precursor resonator structure relative to a plurality of waveguides. The method also includes dividing the precursor resonator structure into a plurality of separate resonators after the precursor resonator structure has been fixed relative to the waveguides. The precursor resonator structure is divided at locations between the waveguides.

25 Claims, 15 Drawing Sheets

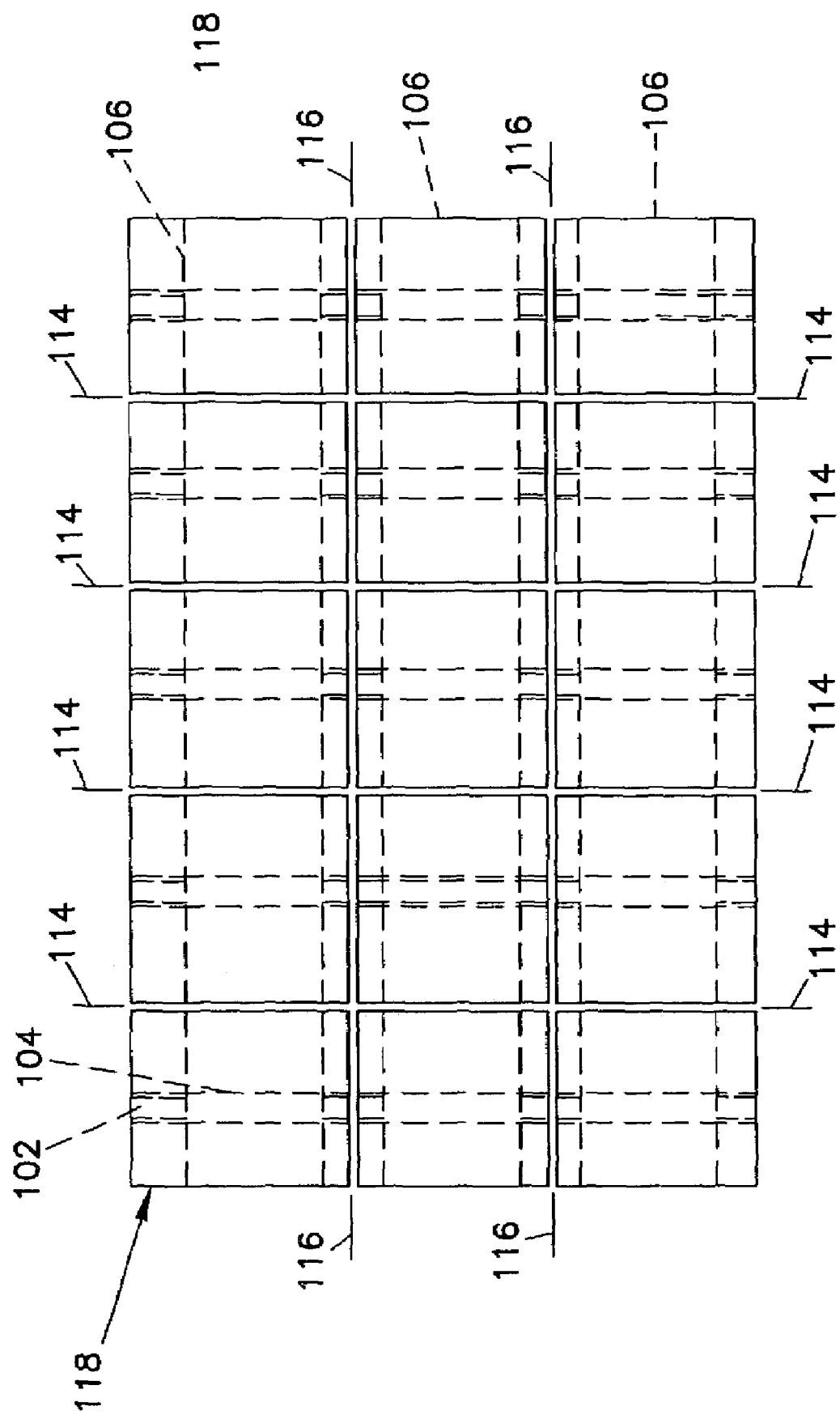

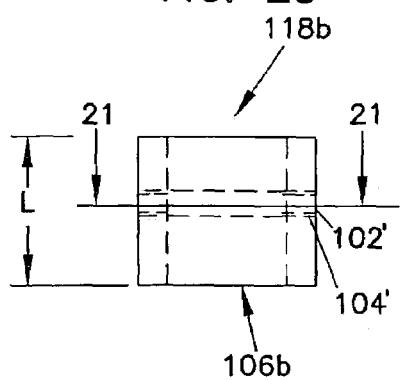
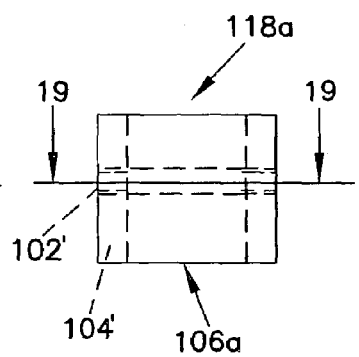
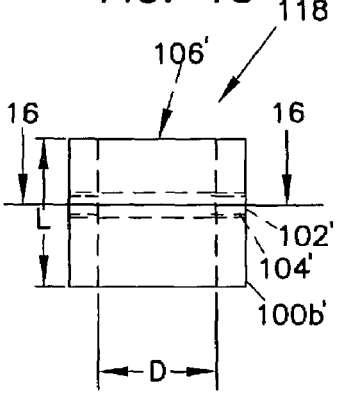
FIG. 20   FIG. 18   FIG. 15
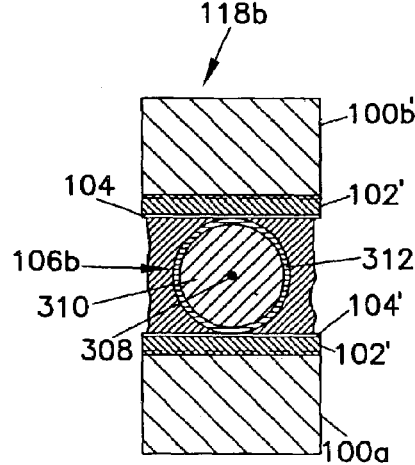
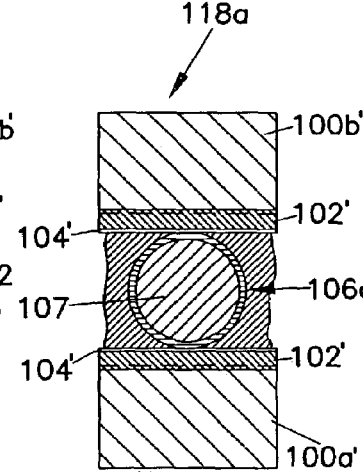
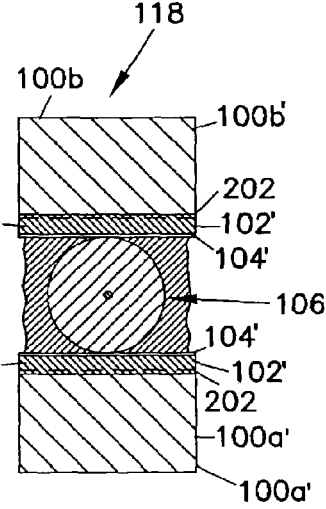
FIG. 21   FIG. 19   FIG. 16

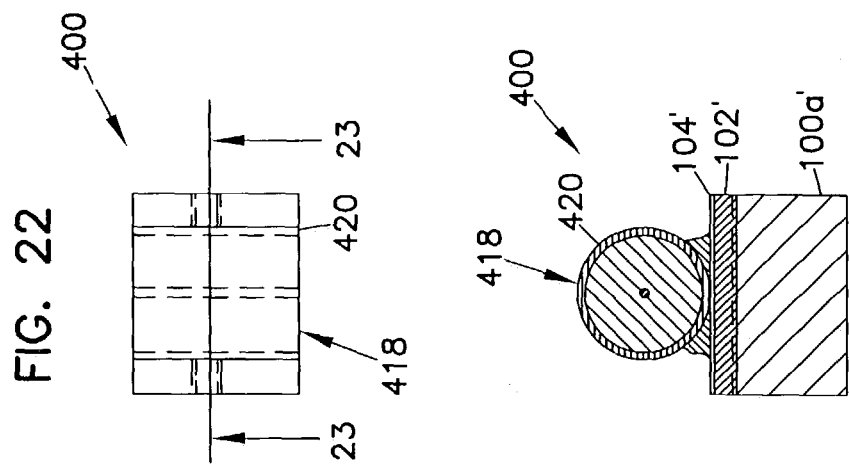
FIG. 22
FIG. 23
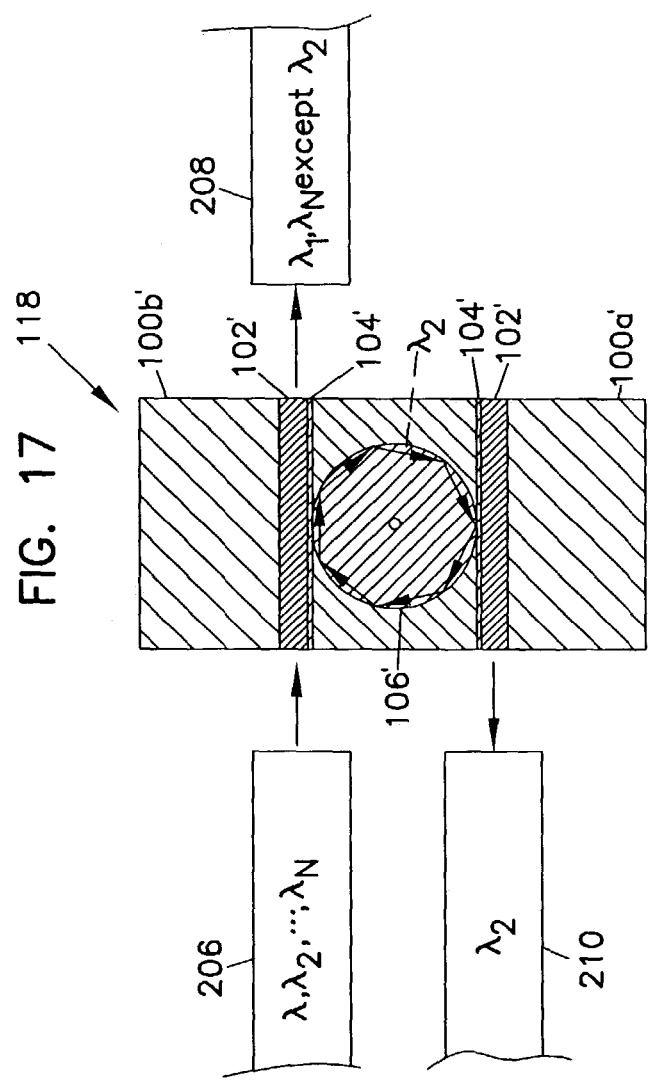
FIG. 17

MICRORING RESONATOR AND METHOD FOR MANUFACTURING

TECHNICAL FIELD

The present disclosure relates generally to ring resonators and methods for fabricating ring resonators.

BACKGROUND

Microring resonators are a class of resonant filter that is receiving increased attention in the technical and business communities. Normally rig resonators include circular or elliptical cavities that can support standing wave resonant modes (i.e., also known as whispering gallery modes) for a wavelength of interest. If such a ring is placed near an optical waveguide which is conveying a stream of several closely-spaced wavelength channels, energy at the resonant wavelength of the ring can be coupled out of the stream without disturbing the other wavelength channels. Example uses for ring resonators include channel-dropping filters, channel-adding filters, non-linear optical applications and sensors.

FIG. 1 shows an example prior art channel-dropping filter 20. The filter 20 includes a ring resonator 22, an input waveguide 24 and an output waveguide 26. The ring 22 is separated from the waveguides 24, 26 by spaces 28. The ring 22 can support a standing wave resonant mode for a channel having a wavelength $\lambda_2$. The ring 22 may also be able to support modes of different wavelengths as well. In use, a stream of closely-spaced wavelength channels ($\lambda_1, \lambda_2, \ldots \lambda_N$) is conveyed through the input waveguide 24 in a direction indicated by arrow 30. As the stream of wavelength channels passes by the ring 22, the resonant wavelength $\lambda_2$ of the ring 22 is separated from the stream of wavelength channels. Specifically, the wavelength channel $\lambda_2$ is coupled out of the stream of wavelength channels $\lambda_1, \lambda_2, \ldots, \lambda_N$ and resonates about the outer surface of the ring 22 as indicated by arrows 32. The standing wavelength channel $\lambda_2$ within the ring 22 is extracted from the ring 22 through the output waveguide 26 as indicated by arrow 34. The net result is that the information being conveyed on the channel $\lambda_2$ is separated from the multichannel stream $\lambda_1, \lambda_2, \ldots, \lambda_N$ without disturbing the other wavelength channels of the stream.

FIG. 2 illustrates a prior art sensor 41 including a waveguide 40 and a resonator ring 42. The ring resonator ring 42 is separated from the waveguide 40 by a space 44. A substrate 46 is provided about the outer surface of the ring 42. The substrate 46 has characteristics which induce or encourage the attachment of a particular type of analyte (e.g., a biological species such as a bacteria or microbe, or a chemical species) which is desired to be defected. Prior to attachment of the analyte on the substrate 46, the ring 42 can support a standing wave resonant mode for a wavelength $\lambda_2$. Thus, the ring 42 is capable of extracting a wavelength channel $\lambda_2$ from a wavelength channel stream $\lambda_1, \lambda_2, \ldots, \lambda_N$ that is conveyed through the waveguide 40. When the analyte attaches (e.g., grows upon, chemically bonds with, or otherwise joins or adheres to) on the substrate 46, the resonant wavelength of the ring 42 shifts such that the ring 42 no longer can support a standing wave resonant mode for the wavelength $\lambda_2$. When this occurs, the wavelength channel $\lambda_2$ is no longer extracted from the channel stream. Instead, a different wavelength is extracted. Detection of this resonant wavelength shift or change in spectrum indicates, the presence of the analyte on the substrate 46.

While ring resonators are simple enough in principle, they can be difficult to fabricate because of the material and dimensional constraints required. A ring resonator frequently is required to have a ring radius in the neighborhood of 10–200 microns. The smoothness of the surface is most important for creating a precise resonance, and ring diameters required for setting the resonance wavelength, are often required to be fabricated and maintained to fractions of a micron. Precision in the separation between the ring resonator and the adjacent channel waveguides is also important to maintain the proper coupling between the ring and the channel. Again, the tolerances can be in the range of fractions of a micron.

The precise tolerances required in the manufacture of microring resonators places extreme demands on the processes used to manufacture ring resonators, especially in achieving the needed wall smoothness, ring dimensions and ring channel separations. Typical fabrication techniques involve planar microelectronic wafer processes such as thin film deposition, photolithography and etching. Because of the high aspect, ratio of the etch that is required, deep reactive ion etching techniques are typically used. Major drawbacks of this approach include the roughness of the etched sidewalls and the difficulty in maintaining precise ring/waveguide separation spacings. Roughness leads to a large amount of scattering loss which leads to broad resonance causing imprecise detection in sensors, and also creates poor optical coupling.

SUMMARY

One inventive aspect of the present disclosure relates to an efficient technique for manufacturing ring resonators.

Another inventive aspect of the present disclosure relates to methods for manufacturing ring resonators using structures such as optical fibers or optical capillaries.

Further inventive aspect of the present disclosure relates to microring resonators manufactured from structures such as optical, fibers, capillaries, or like structures.

Still another inventive aspect of the present disclosure relates to methods for manufacturing ring resonators that provide for increased flexibility in the choice of materials to be used for the resonator rings and channel waveguides.

Still another inventive aspect of the present disclosure relates to a method for, fabric ating ring resonators by dividing or dicing a precursor resonator structure into a plurality of resonator rings.

Examples of a variety of inventive aspects in addition to those described above are set forth in the description that follows. It is to be understood that both the foregoing general description and the following detailed description are exemplary and explanatory only and are not restrictive of the broad inventive aspects that underlie the examples disclosed herein.

BRIEF DESCRIPTION OF THE DRAWINGS

FIG. 14 illustrates the assembly of FIG. 12 after having been cut along cutting planes parallel to the fibers so as to provide a plurality of separate waveguide ring resonator devices;

FIG. 15 is ad top plan view of one of the waveguide ring resonator devices of FIG. 14;

FIG. 16 is a cross-sectional view taken along section line 16—16 of FIG. 15;

FIG. 17 illustrates the waveguide ring resonator device of FIGS. 15 and 16 used as a channel-dropping filter;

FIG. 18 illustrates an alternative waveguide ring resonator device having a ring resonator formed by a length of capillary.

FIG. 19 is a cross-sectional view taken along section 19—19 of FIG. 18;

FIG. 20 is a plan view of an alternative waveguide ring resonator device having a ring resonator defined by a coating provided about an optical fiber;

FIG. 21 is a cross-sectional view taken along section 21—21 of FIG. 20;

FIG. 22 is a top plan view of a ring resonator analyte sensor made in accordance with the principles of the present disclosure;

FIG. 23 is a cross-sectional view taken along section line 23—23 of FIG. 22.

DETAILED DESCRIPTION

Reference will now be made in detail to examples of how certain inventions may be put into practice. Whenever possible, the same reference numbers will be used throughout the drawings to refer to the same or like parts.

One inventive aspect, examples of which are disclosed herein, relates to a method for fabricating ring resonators. The method includes providing a precursor ring resonator structure such as an optical fiber, optical capillary or like structure, and dividing the precursor ring resonator structure into a plurality of pieces to provide a plurality of ring resonators. In a preferred embodiment, the precursor ring resonator structure is positioned at a fixed spacing relative to one or more waveguide structures prior to dividing the precursor ring resonator structure. In other embodiments, the ring resonators divided from the precursor resonator structure can be fixed relative to waveguides after the dividing process.

Another inventive aspect, examples of which are disclosed herein, relates to a method for making a plurality of waveguide ring resonator devices. The method includes providing (e.g., depositing) waveguides on a substrate. The method also includes providing (e.g., depositing) spacer structures over the waveguides. The method further includes positioning precursor ring resonator structures across the waveguides. Finally, the method includes cutting through the substrate and the precursor ring resonator structures at locations between the waveguides to provide a plurality of waveguide ring resonator devices. A more detailed sequence of steps in accordance with the above method is described below with reference to FIGS. 3–14. It will be appreciated that the depicted method steps of FIGS. 3–14 provide examples of how certain inventive aspects may be practiced, but are not intended to limit the scope of the broad underlying inventions.

I. Providing Waveguides on Substrate

Figure 1:
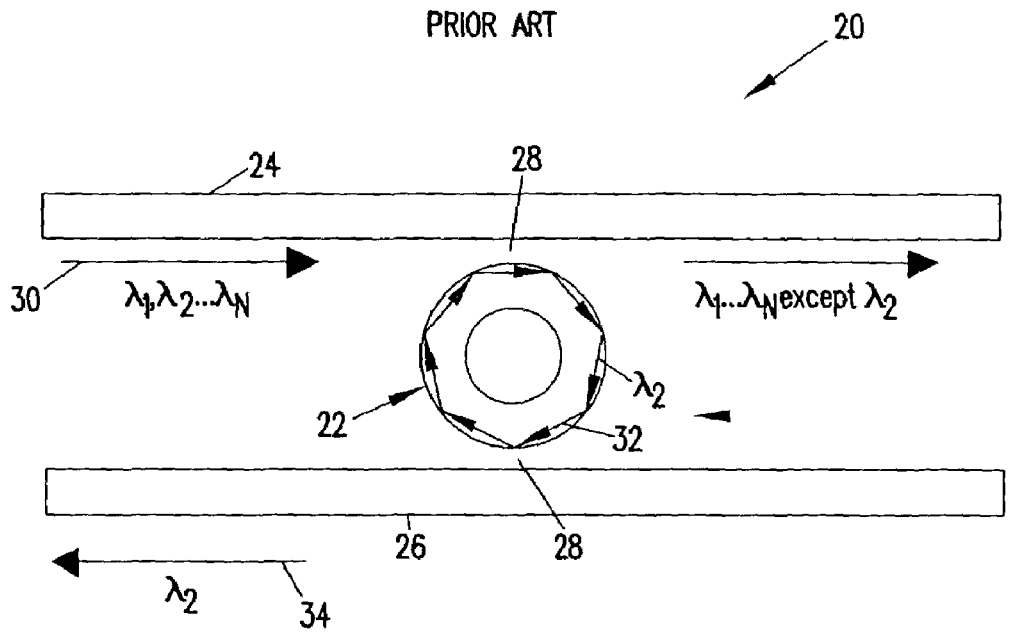
FIG. 1 illustrates a prior art ring resonator channel-dropping filter.
Figure 2:
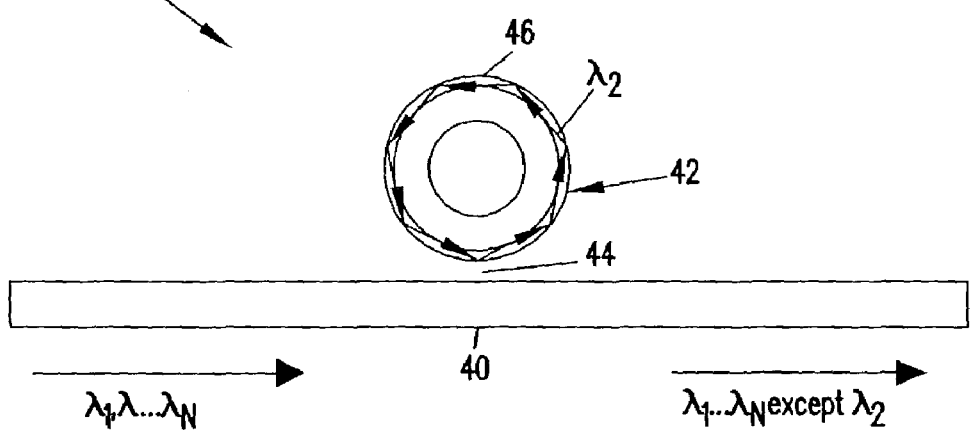
FIG. 2 illustrates a prior art ring resonator analyte sensor.
Figure 3:
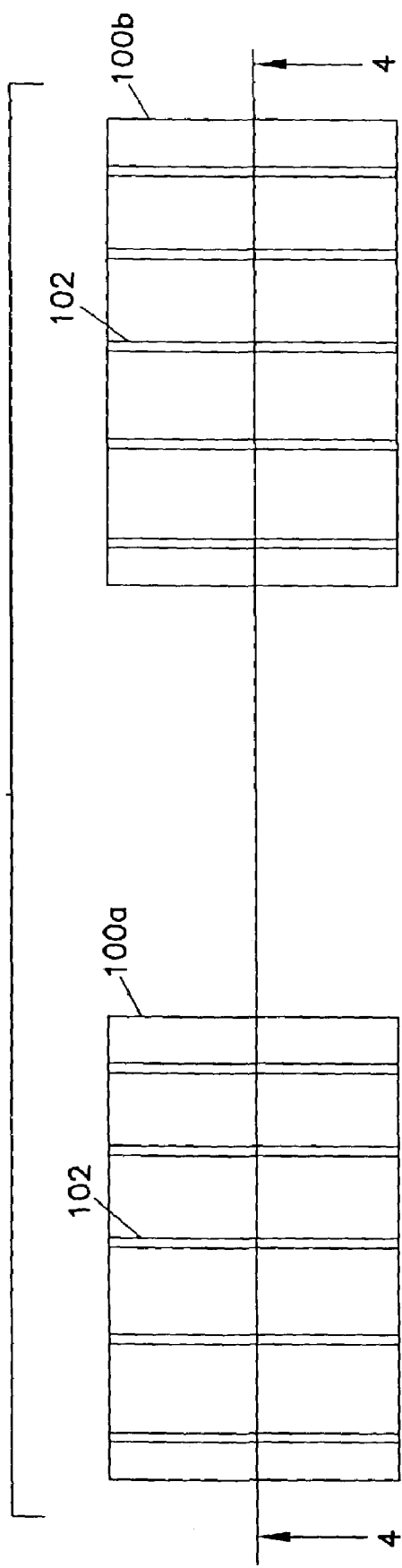
FIG. 3 is a plan view of two substrates having waveguides provided thereon.
Figure 4:
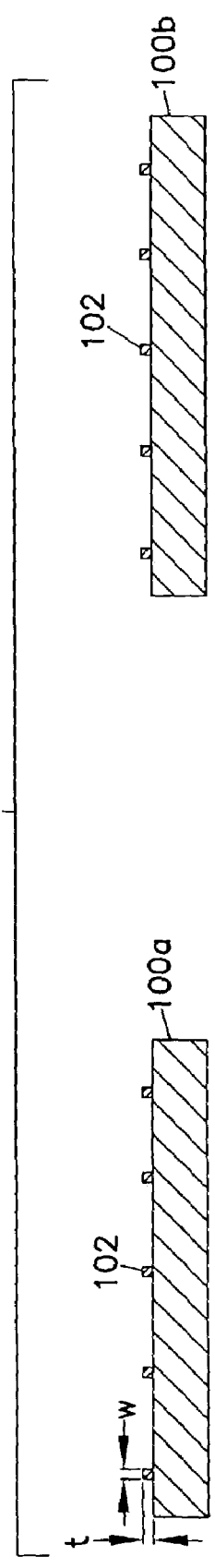
FIG. 4 is a cross-sectional view taken along section line 4—4 of FIG. 3.

FIGS. 3 and 4 illustrate two substrates 100$a$, 100$b$ adapted for supporting one or more waveguides. In a preferred embodiment, the substrates 100$a$, 100$b$ are made of a relatively rigid material having a relatively low refractive index (e.g., an index of refraction less than or equal to 1.45). Example materials of which the substrates 100$a$, 100$b$ may be manufactured include plastic, glass, a silicon wafer having a coating with a low index of refraction, or other like materials.

Referring still to FIGS. 3 and 4, a plurality of waveguides 102 are provided on the top sides of the substrates 100$a$, 100$b$. As depicted in the figures, the waveguides 102 are relatively narrow strips or lines of material arranged in a generally parallel relationship with respect to one another. It will be appreciated that the waveguides 102 can be provided on the substrates by any number of techniques. In one embodiment, the waveguides 102 are provided on the substrate 100 by a deposition technique such as a vapor deposition technique, a sol-gel process, laser writing in a photosensitive medium, or an ion exchange process.

The waveguides 102 preferably have an index of refraction that is higher than the index of refraction of the substrate material. In one non-limiting embodiment, the waveguides 102 each have an index of refraction in the range of 1.50 to 2.7. Example materials for fabricating the waveguides 102 include doped silica, silicon nitride, silicon oxynitride, tin oxide, aluminum oxides, diamond-like carbon, etc. In a non-limiting embodiment, the waveguides 102 each have a thickness t in the range of 1 to 10 micrometers, and a width w in the range of 1–10 microns.

II. Providing Spacer Over Waveguides

Figure 5:
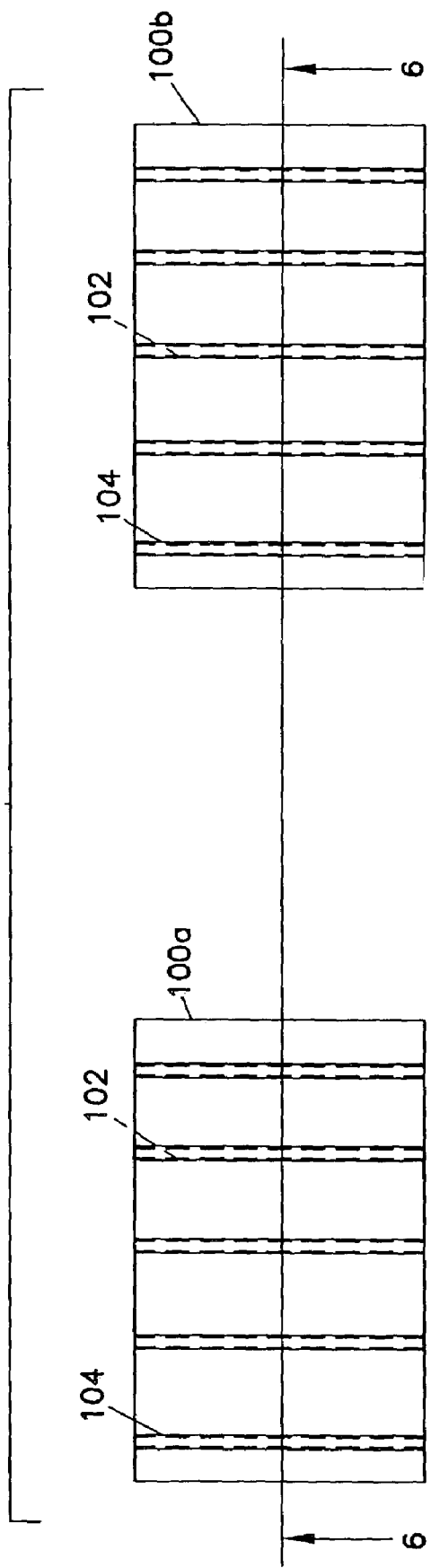
FIG. 5 is a top plan view of the substrates of FIG. 3 with a spacer layer deposited over the top sides of the substrates and over the waveguides.
Figure 6:
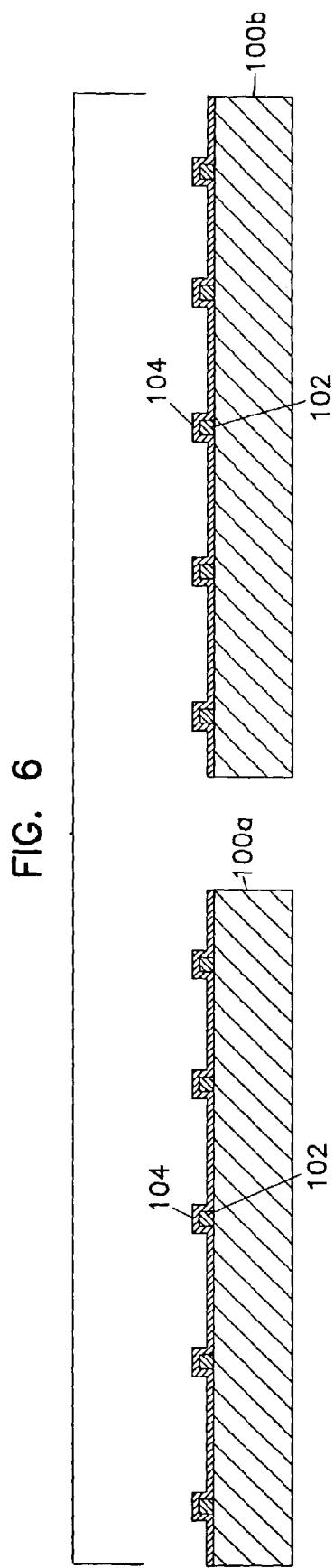
FIG. 6 is a cross-sectional view taken along section line 6—6 of FIG. 5.

Referring to FIGS. 5 and 6, the next step in the manufacturing process involves providing a spacer layer 104 over the waveguides 102. In the depicted embodiment of FIGS. 5 and 6, a spacer layer is provided over the entire top surface of each of the substrates 100$a$, 100$b$. In alternative embodiments it may be desirable to only cover the waveguides 102 without covering the remainder of the substrate 100$a$, 100$b$.

The spacer layer 104 preferably has a lower index of refraction than the waveguides 102, and is also preferably substantially thinner than the thickness of the waveguides 102. In one embodiment, the spacer layer 104 has a thickness in the range of 0.05–2 microns, and an index of refraction in the range of 0.02–2.5 less than the index of the waveguide. In a more preferred embodiment, the thickness of the spacer layer 104 is about 0.1 micron and the index of refraction is about 1.46 for a waveguide having an index of about 1.50. Example materials from which the spacer layer 104 can be made include silicon dioxide and fluorinated glass.

III. Fixing of Precursor Ring Resonator Structures Relative to Waveguides

Figure 7:
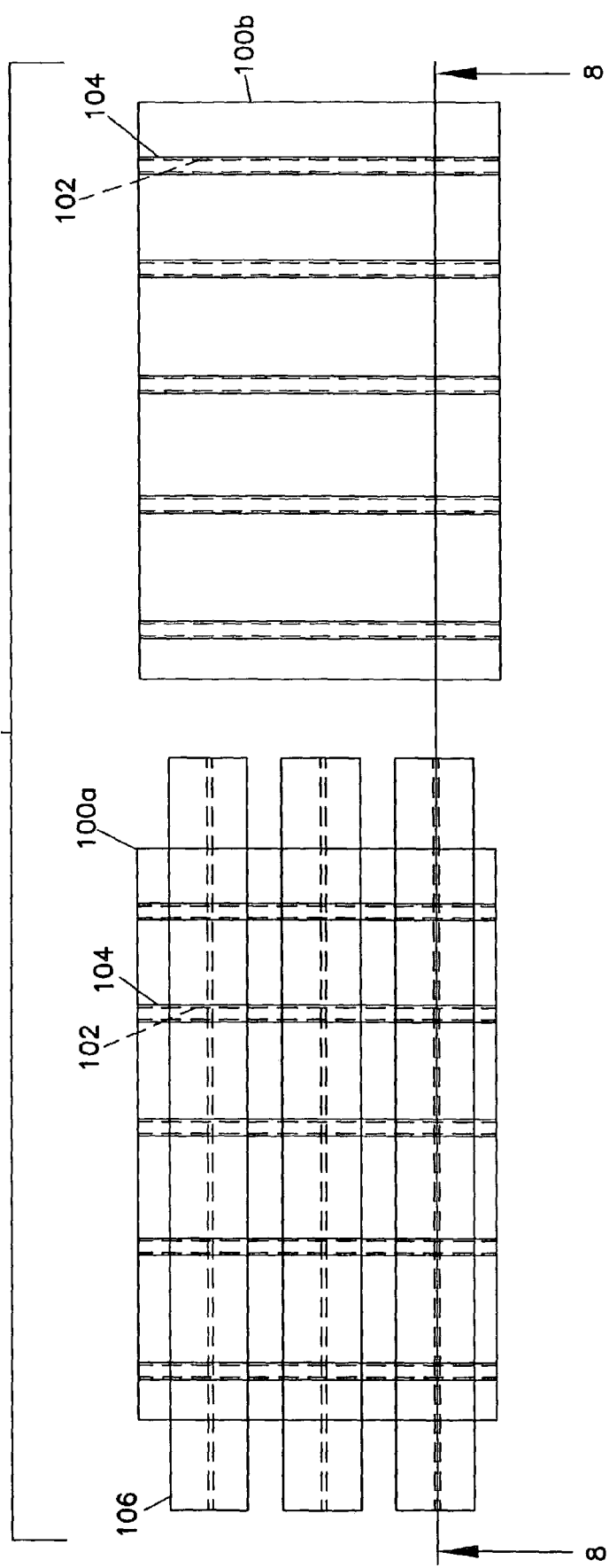
FIG. 7 is a top plan view showing a plurality of optical fibers positioned across the top side of one of the substrates of FIG. 5.
Figure 8:
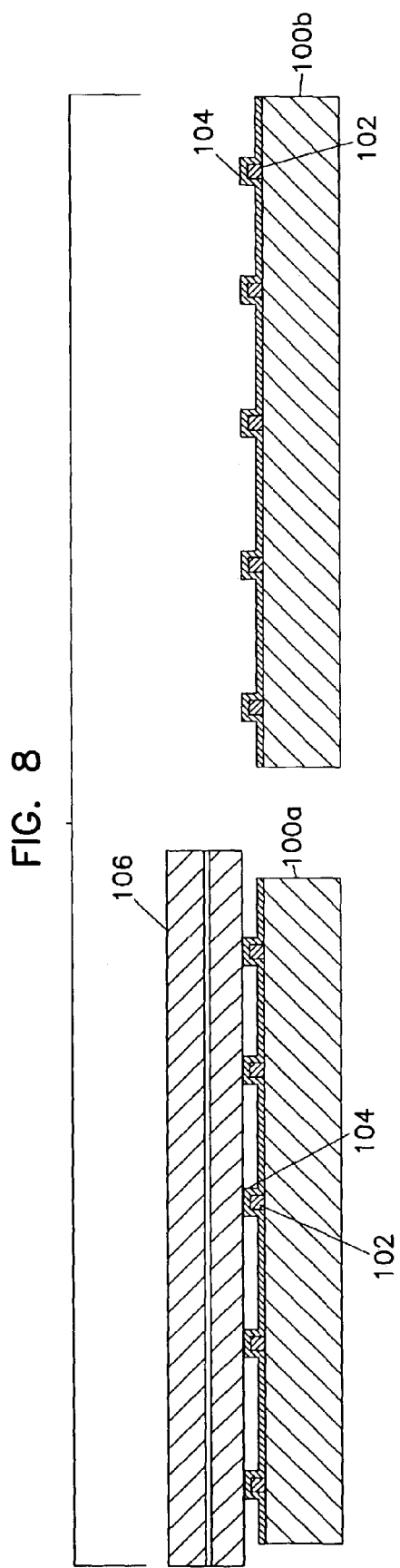
FIG. 8 is a cross-sectional view taken along section line 8—8 of FIG. 7.
Figure 9:
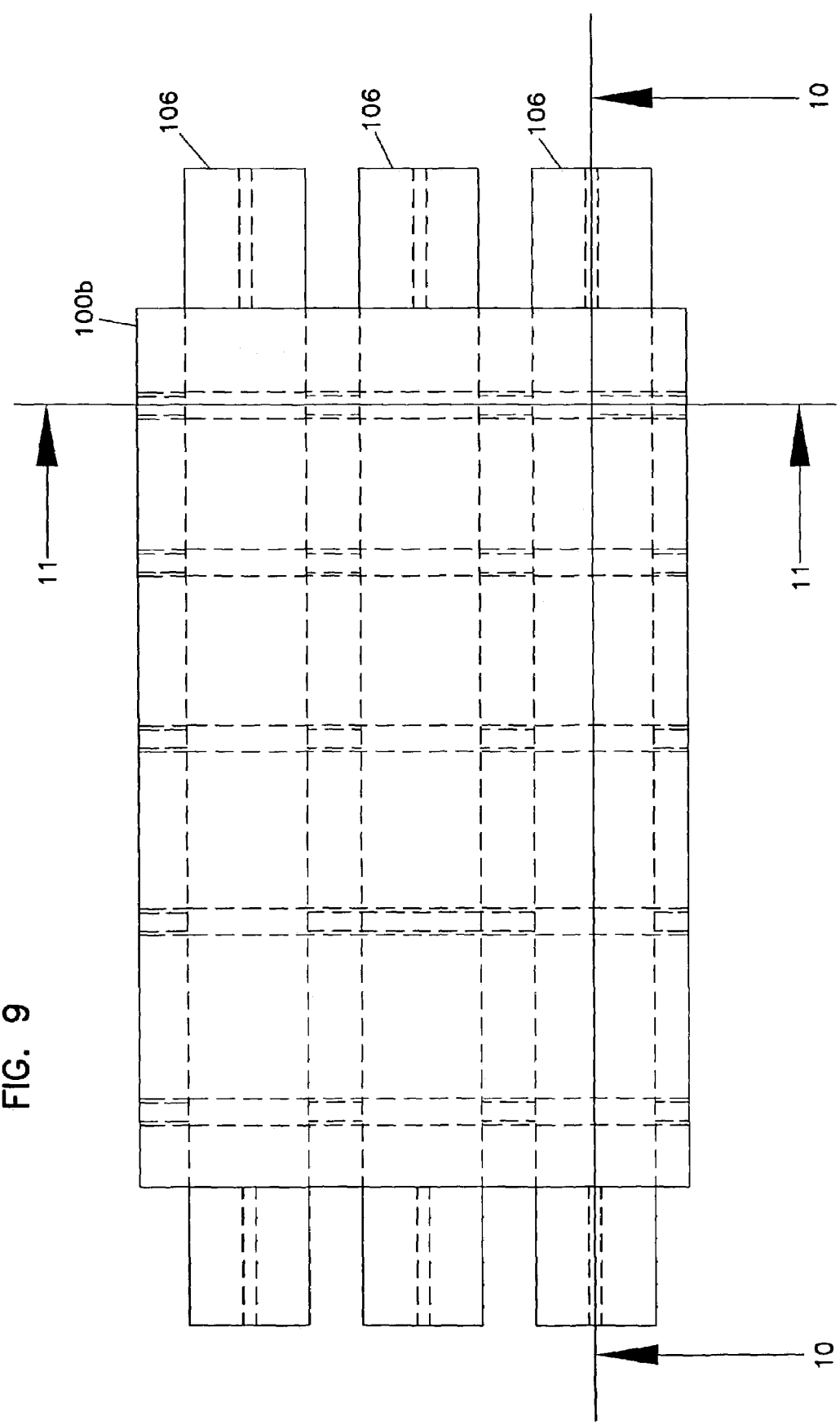
FIG. 9 is a top plan view of an assembly including the fibers of FIG. 7 positioned between the two substrates of FIG. 7.

Once the spacer layers 104 have been provided, one or more precursor ring resonator structures are fixed relative to the waveguides 102. FIGS. 7 and 8 show a plurality of precursor resonator structures in the form of optical fibers 106 that have been positioned across one of the substrates 100a in a direction generally parallel to one another and generally perpendicular relative to the waveguides 102. The waveguides 102 are generally tangentially aligned relative to the fibers 106. As shown in FIG. 8, the fibers 106 are separated from the waveguides 102 by the thickness defined by the spacer layer 104. Preferably, the thickness of the spacer layer 104 is selected to provide optimal optical coupling between the wave guides 102 and the fibers 106 when in use.

Figure 11:
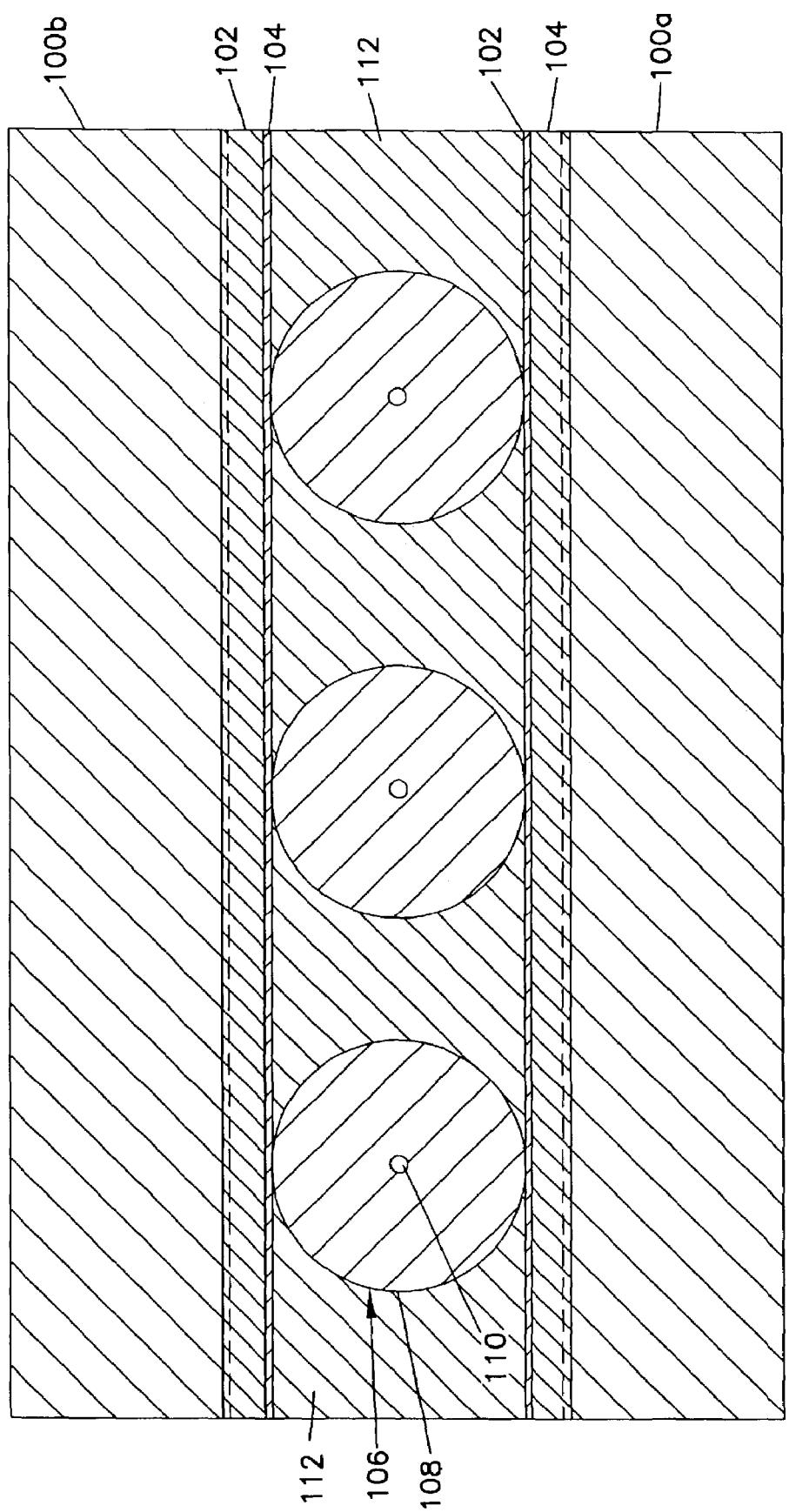
FIG. 11 is a cross-sectional view taken along section line 11—11 of FIG. 9.

In one embodiment, the fibers have been stripped of their outer polymeric coating thereby leaving an outer cladding 108 that surrounds an inner core 110 (see FIG. 11). Typically, the core 110 has a slightly higher index of refraction than the cladding 108. The cladding and core are typically made of materials such as glass or plastic. In one non-limiting embodiment, the cladding includes silica, and the core includes germanium-doped silica. Example diameters for the fibers are in the range of 5–50 microns for the cores and 50–250 microns for the cladding.

It will be appreciated that the fibers 106 can have a circular or non-circular cross section. It is preferred for the outer surface of the fibers 106 to have a higher index of refraction than the spacer layer 104. If the fiber 106 does not have an index of refraction higher than that of the spacer layer 104, a high index coating can be applied about the circumference of the fiber 106 (see the embodiment of FIG. 21). In certain embodiments, the thickness of such coatings can be in the range of 0.1 to 2 microns.

Figure 10:
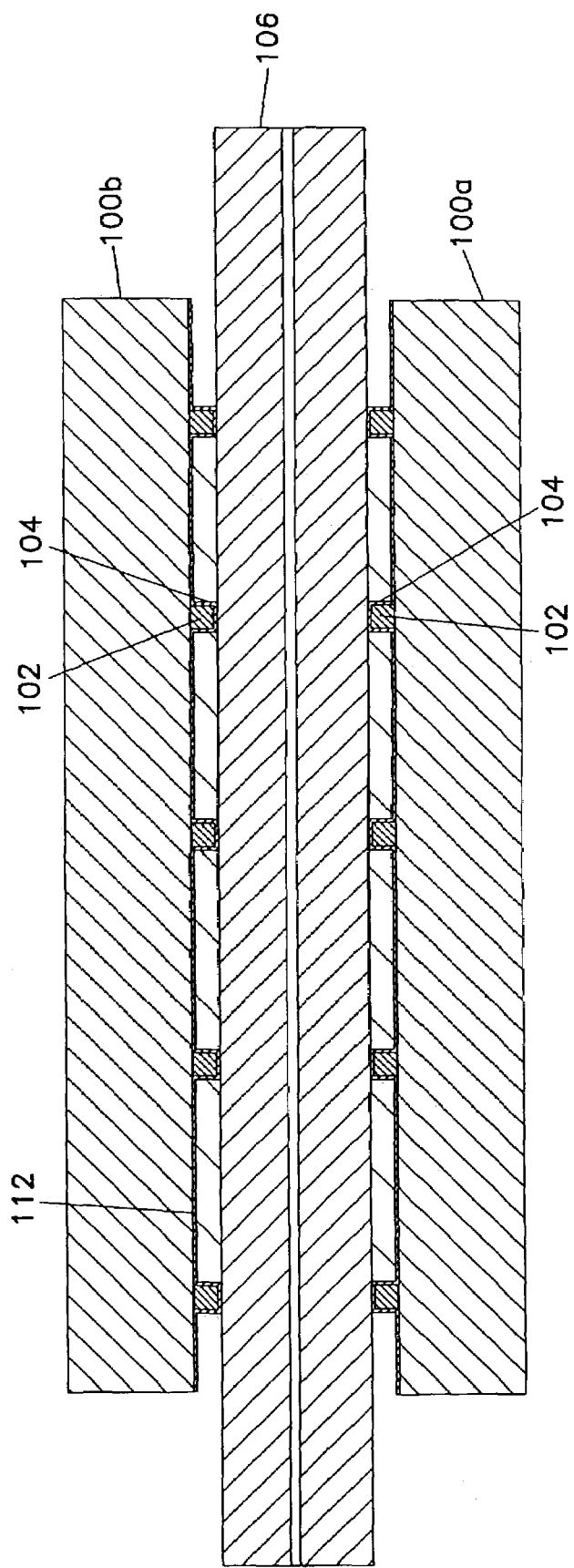
FIG. 10 is a cross-sectional view taken, along section line 10—10 of FIG. 9.

After the fibers 106 have been placed across the top side of substrate 100a, the substrate 100b is positioned over the fibers 106 (see FIGS. 9–11) such that the fibers 106 are sandwiched between the two substrates 100a, 100b. As shown in FIG. 10, the substrate 100b is positioned such that the waveguides 102 of the substrate 100b align with the waveguides 102 of the substrate 100a. As best shown in FIG. 11, the waveguides 102 of the substrate 100a are affixed adjacent to bottom sides of the fibers 106 and the waveguides 102 of the substrate 100b are affixed adjacent to top sides of the fibers 106. The top and bottom sides of the fibers 106 contact the spacer layers 104 and the spacer layers 104 provide a desired spacing between the fibers 106 and the waveguides 102 so as to provide an effective optical coupling between the components when in use.

To secure the entire assembly together, a bonding material 112 is positioned in the void areas between the substrates 100a, 100b as shown in FIG. 11. Example materials for bonding the assembly together include low index acrylates, epoxy adhesives, polymers, gels, low melting glasses, ceramers, etc.

IV. Dividing Assembly into Separate Waveguide Ring Resonator Devices

Figure 12:
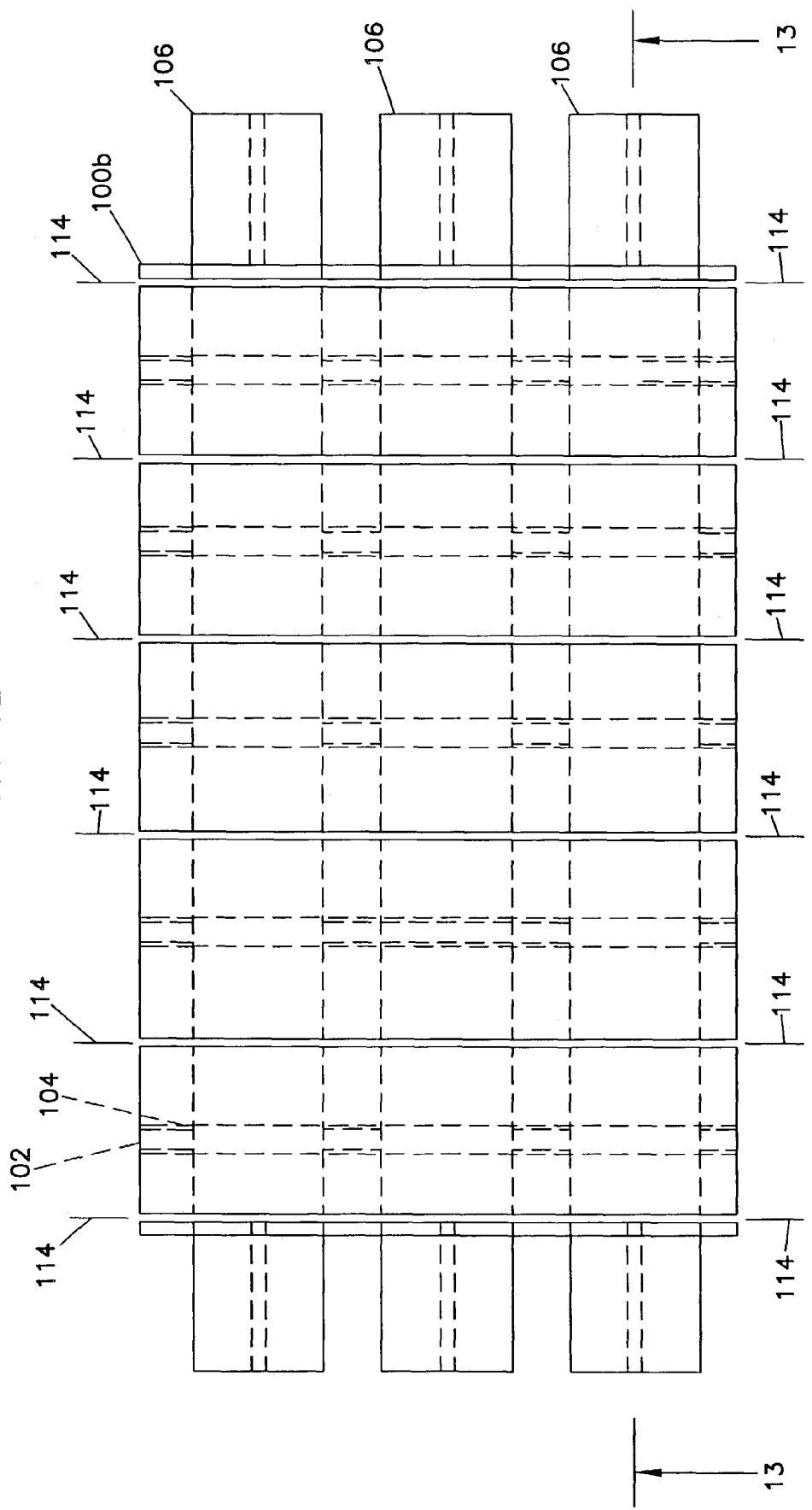
FIG. 12 illustrates the assembly of FIG. 9 after having been cut into separate pieces along cutting planes located between the waveguides of the assembly.
Figure 13:
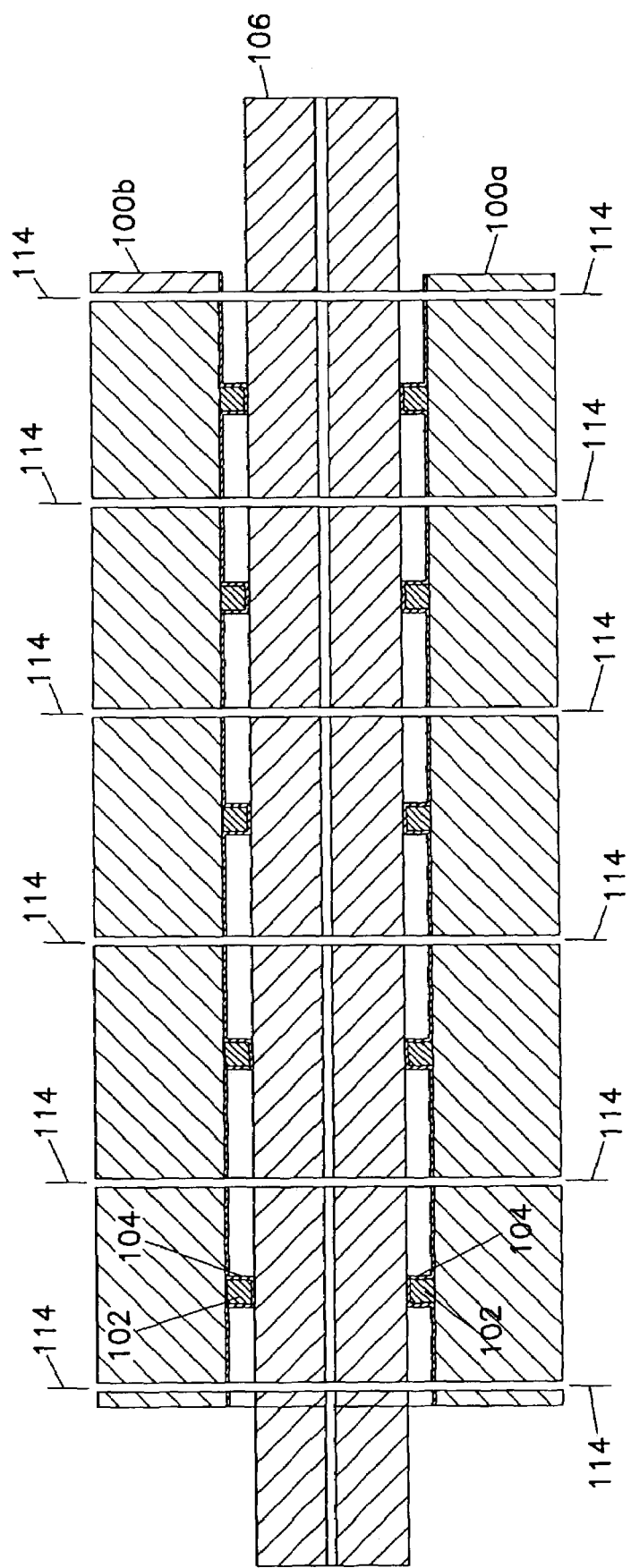
FIG. 13 is a cross-sectional view taken along section line 13—13 of FIG. 12.

Once the assembly of substrates 100a, 100b, and fibers 106 has been bonded together, the assembly is preferably divided into a plurality of pieces as shown in FIGS. 12–14. For example, the assembly can be divided along division lines 114 that extend in a direction generally transverse to the longitudinal axes of the fibers 106. The division lines 114 are generally parallel to the waveguides 102, and with the exception of the division lines at the ends of the assembly, are located between adjacent waveguides 102.

FIG. 14 shows the assembly further divided along division lines 116 that extend generally parallel to, the fibers 106. The division lines 116 are positioned between the fibers 106 and cut through the waveguides 102. The assembly is preferably divided along division lines 114 and 116 using a low impact, abrasive technique. For example, the division lines 114 and 116 can be provided by cutting the assembly with a low impact, abrasive saw. Other dividing/cutting techniques include lasers, water jets, etc.

The combination of division lines 114 and 116 provides a plurality of separate pieces each forming a waveguide ring resonator device 118. Each of the ring resonator devices 118 includes a portion of one of the fibers 106 that functions as a ring resonator. FIGS. 15 and 16 show one of the ring resonator devices 118 that was divided from the assembly of FIG. 14. The device 118 includes substrates 100a', 100b' divided from substrates 100a, 100b, waveguides 102' divided from waveguides 102, spacer layers 104' divided from spacer layers 104 and a ring resonator 106' divided from one of the fibers 106. Opposite sides of the ring resonator 106' are coupled to the waveguides 102'. In a non-limiting embodiment, ring resonator 106' as a diameter D in the range of 50–250 microns and an axial length L in the range of 2–2000 microns.

In the depicted embodiment, the assembly is sliced and diced such that each resultant waveguide resonator device 118 has a single ring resonator 106'. In alternative embodiments, it may be desirable to only provide the division lines 114. By not cutting the assembly along lines 116, waveguide resonator devices having multiple resonator rings positioned between a pair of waveguides can be manufactured.

Because the above manufacturing technique involves the deposition of materials, the choice of materials is considerably more flexible than the materials available pursuant to deep reactive ion etching techniques. Further, by vapor-depositing the spacer layers 104, the thickness of the spacer layers can be precisely controlled. Moreover, in alternative embodiments, the spacer layers 104 can be patterned to get different spacing layer thicknesses corresponding to different portions of the precursor resonator structures 106. It is also contemplated to utilize fibers of different diameters as precursor ring resonators. Moreover, while the above manufacturing process involves the use of a plurality of precursor resonator structures 106 arranged parallel to one another, in alternative embodiments, only a single precursor resonator structure may be used, or a plurality of structures could be aligned in a non-parallel relationship. By using fibers of different diameters, ring resonators having different resonant wavelengths can be made. Moreover, fibers having different diameters can be placed side by side on a precursor waveguide structure, and diced to form microring devices each having multiple ring resonators of different diameter arranged in series along the waveguide (see FIG. 24).

V. Finishing the Waveguide Ring Resonator Devices

After the assembly has been divided into the individual waveguide ring resonator devices 118, end surfaces 200, 202 (labeled in FIG. 16) of the pieces 118 can be lapped and polished to prepare for connection to optical fibers. To facilitate handling of the pieces during the final surface finishing, carrier substrates can be affixed to one or both of the substrates 100a' and 100b'. In certain embodiments, grooves or other alignment structures can be further provided in the substrates 100a', 100b' to facilitate connecting optical fibers to the waveguides 102' of the waveguide resonator devices 118'.

VI. Example Use of Waveguide Ring Resonator Device

FIG. 17 schematically shows one of the waveguide resonator devices 118 functioning as a channel-dropping filter. As shown in FIG. 17, the waveguide 102' of the substrate 100b' is optically coupled to an input fiber 206 and an output fiber 208. Also, the waveguide 102' of the substrate 100a' is optically coupled to an output fiber 210. The input fiber 206 conveys a stream of signals having wavelengths $\lambda_1, \lambda_2, \ldots \lambda_N$ into the waveguide 102 of the substrate 100b'. The ring resonator 106' of the device 118 can support a standing wave resonant mode for a signal channel having a wavelength $\lambda_2$ and possibly other wavelengths as well. In use, a channel wavelength $\lambda_2$ in the stream of signals being conveyed through the waveguide 102 of the substrate 100b' will be coupled to the ring resonator 106'. When coupled to the ring resonator 106', the wavelength channel $\lambda_2$ generates a standing wave about the outer surface of the ring resonator 106'. The standing wave supported at the ring resonator 106' is coupled to the waveguide 102 of the substrate 100a'. Thus, information conveyed on the wavelength $\lambda_2$ is effectively separated from the multi-channel stream of the input fiber 206 and directed into fiber 210.

As indicated above, the outer surface of the ring resonator 106' supports a standing wave having the resonant wavelength $\lambda_2$. As previously described, the ring resonator 106' is preferably made from a precursor resonator structure manufactured using a material drawing process. For example, the precursor resonator structure can be manufactured by drawing a material such as plastic or glass to form an elongated precursor ring resonator structure. In certain embodiments, the ring resonator 106' can be made from a portion of a length of drawn optical fiber, or a portion of a length of drawn optical capillary. These types of structures have relatively smooth outer surfaces. Therefore, when the standing wave is supported on the outer surface, the signal encounters minimal scattering.

As used herein, the term "ring resonator" is not limited to structures having circular or annular cross-sections, but instead includes any structure or shape capable of supporting a standing wave about its perimeter.

VII. Alternative Devices

FIGS. 18 and 19 illustrate an alternative waveguide resonator device 118a that is an example of how inventive aspects in accordance with the present disclosure may be put into practice. The waveguide ring resonator device 118a has the same configuration as the waveguide resonator device 118, except ring resonator 106a is formed from a length of optical capillary instead of a length of optical fiber 106'. Similar to the embodiments of FIGS. 15 and 16, the waveguide resonator device 118a has substrates 100a', 100b', waveguides 102' and spacer layers 104'. It will be appreciated that the waveguide resonator device 118a can be manufactured in accordance with the same principles utilized to manufacture the waveguide resonant air device 118, except that capillaries are used as the precursor resonator structures instead of optical fibers 106.

Referring still to FIG. 19, the interior of the resonator 106a can be filled with a material 107 such as liquid crystal or a polymer whose refractive index can be modified by an applied field, thereby tuning the resonance wavelength/frequency of the resonator 106a.

FIGS. 20 and 21 illustrate another waveguide resonator device 118b that is an example of how inventive aspects in accordance with the present disclosure may be put into practice. The waveguide resonator device 118b has the same configuration as the waveguide resonator device 118, except that a ring resonator 106b in the form of a coated length of optical fiber has been substituted for the bare fiber ring resonator. The coated fiber includes a center core 308, a cladding 310, and an outer coating; 12 made of a material having a relatively high index of refraction. Similar to the previous embodiments, the coated fiber is fixed adjacent to waveguides 102' supported by substrates 100a' and 100b'. Spacer layers 104' provide a desired spacing between the coated fiber and the waveguides 102' so as to provide an optical coupling between the components in use. It is desirable to utilize a high index of refraction coating on the fiber in situations where the index of refraction of the spacer layer 104' is comparable to the index of refraction of the cladding 310 of the optical fiber. By coating the optical fiber with a high index layer, a standing wave will be essentially confined to the coating of the fiber of the ring resonator.

The coating 312 extends about the entire circumference of the cladding 310, and can have an axial length that is equal to the length L of the fiber. Alternatively, the coating 312 can have a length shorter than the, length of the fiber to confine the standing wave mode in an axial direction.

It will be appreciated at the waveguide resonator device of FIGS. 21 and 22 can be manufactured using the same technique employed to manufacture the waveguide resonator device 118, except that coated fibers will be used as the precursor resonator structures as compared to non-coated fibers.

FIGS. 22 and 23 illustrate a sensor 400 that is a further example of how an inventive aspects in accordance with the principles of the present disclosure may be put into practice. This embodiment demonstrates that for a sensor embodiment, it is preferred to have only one waveguide. This type of configuration leaves sufficient exposed space on the waveguide for attachment of an analyte. Variations in the resonance wavelength of the microring resonator can be detected by monitoring variations in the spectral transmission of the input fiber.

The sensor 400 includes a waveguide 102' supported on substrate 100a'. The sensor 400 also includes a ring resonator 418 made from a piece of optical fiber coated with an outer layer 420 conducive to the attachment of a particular analyte (e.g., a biological or chemical species). Alternatively, the ring resonator 418 could be made from other materials such as an, optical capillary coated with layer 420. Example materials for forming the layer 420 include biotin, specific antibodies, streptavidin, etc.

The ring resonator 418 is separated from the waveguide 102' by the spacer layer 104'. The thickness of the spacer layer 104' is selected such that the ring resonator 418 is efficiently optically coupled to the waveguide 102' when in use.

In use, a stream of signals having varying wavelengths can be input through the waveguide 102'. Signals having the resonant wavelength of the ring resonator 418 are extracted, from the signal stream and cause a standing wave to be generated within the layer 420 about the ring resonator 418. In the event an analyte attaches on the outer surface of the ring resonator 418, the resonance wavelength of the ring resonator 418 will shift such that the original resonant wavelength of the ring resonator is no longer extracted from the channel stream, thereby signaling the presence of the analyte. This can be sensed by observing differences in the spectral shape of the output stream of the waveguide 102'.

It will be appreciated that the sensor 400 can be manufactured using techniques similar to those previously described. By way of example the sensor 400 can be manufactured by first depositing waveguides on a substrate. Next, a spacer layer is positioned/over the waveguides. Thereafter, one or more optical fibers having outer surfaces suitable for inducing analyte attachment are positioned across the waveguides. The spacer layers separate the fibers from the waveguides at a distance suitable for providing an optical coupling between the fibers and the waveguides when in use. The optical fibers can then be bonded to the substrate. Once the optical fibers have been bonded in place, a temporary substrate can be placed over the fibers to provide additional support during subsequent cutting operations. With the temporary substrate in place the assembly is preferably cut into a plurality of pieces, with each of the pieces forming a separate sensor device.

Figure 24:
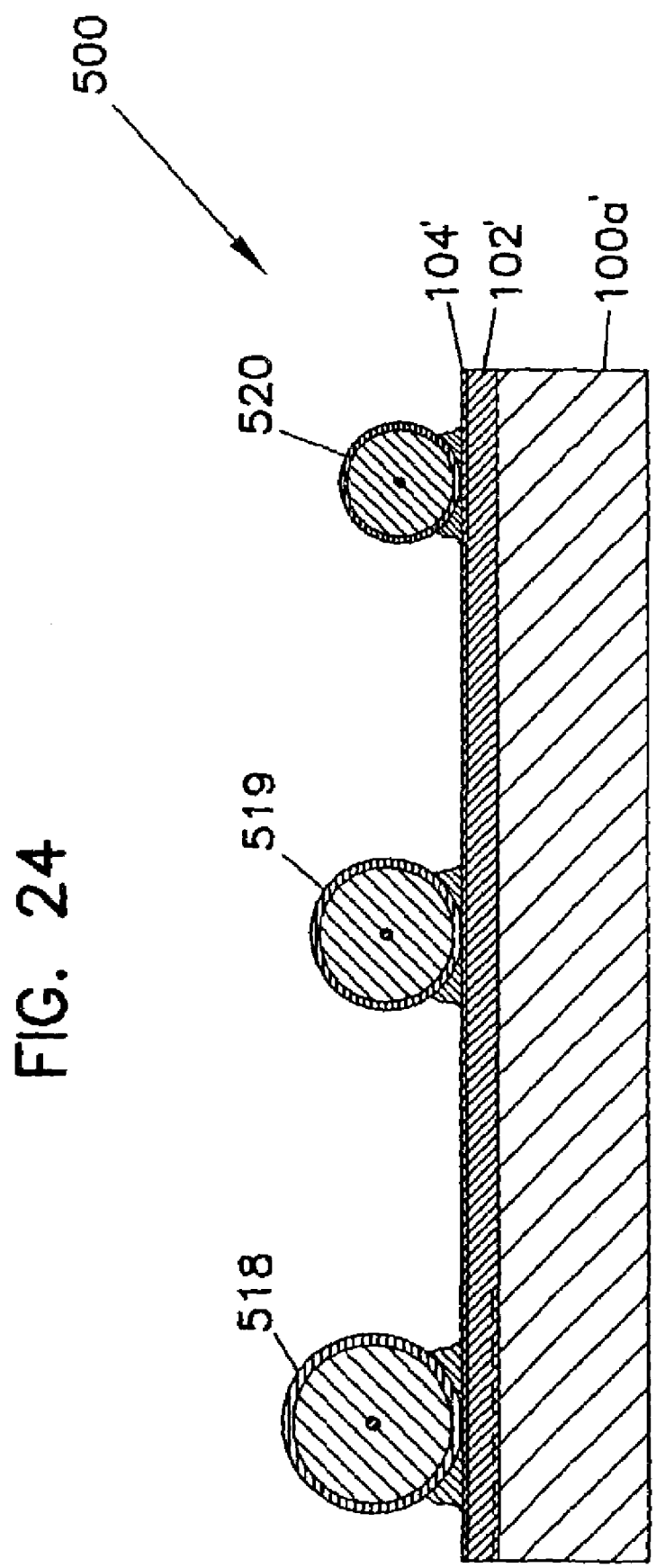
FIG. 24 is a cross-sectional view of an alternative analyte sensor including several ring resonators positioned in series.

FIG. 24 shows another sensor 500 including a waveguide 102' supported on at spacer layer 104' deposited on a substrate 100a'. The sensor includes a plurality of ring resonators 518,519,520 positioned in series along the waveguide 102'. The ring resonators 518,519,520 have different diameters and thus different resonant wavelengths. The ring resonators 518,519,520 can be used to indicate the presence/attachment of different types of analytes. Attachment of analytes to the ring resonators 518,519,520 can be determined by observing/monitoring differences in the spectral shape of the output stream of the waveguide 102'.

It will be appreciated that the device can be efficiently manufactured using techniques similar to those described above. For example, the device 500 can be manufactured by mounting parallel fibers of multiple diameters across a precursor waveguide structure, and then dicing the assembly in a direction perpendicular to the lengths of the fibers.

With regard to the foregoing description, it is to be understood that changes may be made in detail, especially with respect to the shape, size, and arrangement of the parts. It is intended that the specification and depicted features be considered illustrative only and not limiting with respect to the broad underlying concepts of the present disclosure.

What is claimed is:

1. A method for making a plurality of waveguide resonator devices, the method comprising:
   positioning a precursor resonator structure at a fixed separation from a plurality of waveguides; and
   after the precursor resonator structure has been positioned relative to the waveguides dividing the precursor resonator structure into a plurality of separate resonators, the precursor resonator structure being divided at locations between the waveguides.

2. The method of claim 1, wherein the precursor resonator structure is divided by cutting the precursor resonator structure at locations between the waveguides.

3. The method of claim 2, wherein the precursor resonator structure is mechanically cut with an abrasive tool.

4. The method of claim 3, wherein the abrasive tool is a wire saw.

5. The method of claim 1, wherein the precursor resonator structure is elongated.

6. The method of claim 5, wherein the precursor resonator structure is cylindrical.

7. The method of claim 5, wherein the precursor resonator structure is tubular.

8. The method of claim 5, wherein the precursor resonator structure is cut at a plurality of locations spaced-apart along a longitudinal axis of the precursor resonator structure.

9. The method of claim 1, wherein the precursor resonator structure includes drawn glass or plastic.

10. The method of claim 1, wherein the precursor resonator structure includes an optical fiber.

11. The method of claim 1, wherein the precursor resonator structure includes a glass or plastic capillary.

12. The method of claim 1, further comprising depositing the waveguides on a substrate, depositing a spacer layer over the waveguides, and fixing the precursor resonator structure relative to the waveguides by securing the precursor resonator structure to the spacer layer.

13. The method of claim 1, wherein the precursor resonator structure is positioned at a fixed spacing relative to a plurality of sets of waveguides, and wherein the precursor resonator structure is divided at locations between the sets of waveguides such that the separate resonators are coupled to separate sets of waveguides.

14. A method for fabricating a plurality of waveguide resonator devices, the method comprising:
   providing a substrate supporting a plurality of waveguides;
   providing spacer layers;
   mounting a precursor resonator structure to the substrate with the precursor resonator structure extending across the waveguides and separated from the waveguides by the spacer layers; and
   cutting the precursor resonator structure and the substrate into a plurality of pieces to provide a plurality of ring resonator devices, each of the ring resonator devices including a portion of the substrate, a portion of the precursor resonator structure, at least one of the waveguides and at least one of the spacer layers.

15. The method of claim 14, wherein the precursor resonator structure comprises an optical fiber.

16. The method of claim 14, wherein the precursor resonator structure comprises a capillary.

17. The method of claim 14, wherein the precursor resonator structure comprises a coated optical fiber.

18. The method of claim 14, wherein the precursor resonator structure comprises an optical fiber coated with a material adapted to encourage bacterial growth.

19. The method of claim 14, wherein the precursor resonator structure comprises a tube filled with a material having a refractive index that can be modified with an applied field.

20. The method of claim 14, wherein the precursor resonator structure and the substrate are cut with straight cuts located between the waveguides.

21. The method of claim 20, wherein the straight cuts are generally perpendicular to a longitudinal axis of the precursor resonator structure.

22. The method of claim 14, wherein the spacer layers have thicknesses in the range of 0.05–2 microns.

23. The method of claim 14, wherein the spacer layers include a material selected from the group comprising silicon dioxide or fluorinated glass.

24. The method of claim 14, wherein the precursor resonator structure and the substrate are cut with a saw.

25. A method for fabricating a plurality of waveguide resonator devices, the method comprising:
   providing a first substrate supporting a plurality of first waveguides;
   providing a second substrate supporting a plurality of second waveguides;
   providing spacer layers;
   mounting a precursor resonator structure between the first and second substrates with the precursor resonator structure extending across the waveguides and separated from the waveguides by the spacer layers; and
   cutting the precursor resonator structure and the first and second substrates into a plurality of pieces to provide the plurality of ring resonator devices, each of the ring resonator devices including a portion of the first substrate, a portion of the second substrate, a portion of the precursor resonator structure, at least two of the waveguides and at least two of the spacer layers.

* * * * *

UNITED STATES PATENT AND TRADEMARK OFFICE
CERTIFICATE OF CORRECTION

PATENT NO. : 7,062,118 B2
APPLICATION NO. : 10/623215
DATED : June 13, 2006
INVENTOR(S) : Raymond C. Chiu It is certified that error appears in the above-identified patent and that said Letters Patent is hereby corrected as shown below:

Column 1
Line 13, delete "Normally rig" and insert -- Normally, ring --, therefor.
Line 53, delete "defected." and insert -- detected. --, therefor.
Line 66, after "indicates" delete ",".

Column 2
Line 21, delete "aspect, ratio" and insert -- aspect ratio --, therefore.
Line 39, delete "optical, fibers" and insert -- optical fibers --, therefor.
Line 45, delete "for, fabric ating" and insert -- for fabricating --, therefor.

Column 3
Line 11, delete "taken, along" and insert -- taken along --, therefor.
Line 24 (APPROXIMATELY), delete "ad" and insert -- a --, therefor.

Column 4
Line 57, before "it may be" insert -- , --.

Column 6
Line 26, delete "as" and insert -- has --, therefor.

Column 8
Line 4, delete "coating; 12" and insert -- coating 312 --, therefor.
Line 19, delete "the, length" and insert -- the length --, therefor.
Line 42, delete "an, optical" and insert -- an optical --, therefor.
Line 63, after "example" insert -- , --.
Line 65, delete "positioned/over" and insert -- positioned over --, therefor.

Column 9
Line 8, delete "place the" and insert -- place, the --, therefor.
Line 12, after "supported on" delete "at" and insert -- a --, therefor.

UNITED STATES PATENT AND TRADEMARK OFFICE
CERTIFICATE OF CORRECTION

PATENT NO. : 7,062,118 B2
APPLICATION NO. : 10/623215
DATED : June 13, 2006
INVENTOR(S) : Raymond C. Chiu It is certified that error appears in the above-identified patent and that said Letters Patent is hereby corrected as shown below:

<u>Column 9</u>
Line 29, delete "size, and" and insert -- size and --, therefor.
Line 38, in Claim 1, after "waveguides" insert -- , --.

Signed and Sealed this

Tenth Day of October, 2006

JON W. DUDAS
*Director of the United States Patent and Trademark Office*